(12) United States Patent
Weber et al.

(10) Patent No.: US 7,373,826 B2
(45) Date of Patent: May 20, 2008

(54) METHOD FOR MANUFACTURING A FLUID PRESSURE MEASUREMENT UNIT AND A COMPONENT FOR BEING USED IN A FLUID PRESSURE MEASUREMENT UNIT

(75) Inventors: Joerg Weber, Edling (DE); Bernd Beck, Rangendingen (DE)

(73) Assignee: Smiths Medical Deutschland GmbH, Kirchseeon (DE)

( * ) Notice: Subject to any disclaimer, the term of this patent is extended or adjusted under 35 U.S.C. 154(b) by 0 days.

(21) Appl. No.: 11/458,961

(22) Filed: Jul. 20, 2006

(65) Prior Publication Data

US 2007/0209449 A1 Sep. 13, 2007

(30) Foreign Application Priority Data

Feb. 24, 2006 (DE) .................. 10 2006 008 752

(51) Int. Cl.
*A61B 5/02* (2006.01)
(52) U.S. Cl. ........................ 73/700; 600/488
(58) Field of Classification Search ............... 73/700; 600/488
See application file for complete search history.

(56) References Cited

FOREIGN PATENT DOCUMENTS

| EP | 0124308 | 1/1988 |
|----|---------|--------|
| EP | 0180662 | 2/1989 |
| EP | 0360286 | 3/1990 |
| EP | 0232142 | 11/1992 |
| EP | DE4400941 | 4/1995 |
| EP | 0949494 | 10/1999 |

*Primary Examiner*—Andre J. Allen
(74) *Attorney, Agent, or Firm*—Glenn Patent Group; Michael A. Glenn (57) ABSTRACT

A fluid pressure measurement unit is manufactured by steps of providing a measurement element with a measurement chip arranged on a first chip carrier side and a plurality of socket-shaped terminal contacts for contacting contact terminals of the measurement chip, the socket-shaped terminal contacts protruding from a second chip carrier side opposite from the chip carrier first side; providing a housing element comprising a plurality of receiving holes in a housing element first side which are implemented to receive the socket-shaped terminal contacts when combining the housing element with the measurement element, wherein the receiving holes extend from the housing element first side to a housing element second side opposite from the housing element first side; and combining the measurement element and the housing element, wherein the second chip carrier side is opposite from the housing element first side and the socket-shaped terminal contacts are arranged in the receiving holes.

19 Claims, 6 Drawing Sheets

METHOD FOR MANUFACTURING A FLUID PRESSURE MEASUREMENT UNIT AND A COMPONENT FOR BEING USED IN A FLUID PRESSURE MEASUREMENT UNIT

CROSS-REFERENCE TO RELATED APPLICATION

This application claims priority from German Patent Application No. 102006008752.6, which was filed on Feb. 24, 2006, and is incorporated herein by reference in its entirety.

BACKGROUND OF THE INVENTION

1. Field of the Invention

The present invention relates to the technical field of fluid pressure measurement and in particular to the manufacturing of a component for a fluid pressure measurement unit, like, e.g., those used for blood pressure measurement by pressure transmission by means of a liquid column, like the liquid in a pressure measurement tube or a pressure measurement line, respectively.

2. Description of Related Art

In order to cause the least possible effort in hospitals or clinics in the care of patients, there is an increasing interest in combining different measurement and diagnosis systems with each other, in order to hereby on the one hand deal with an excessive fear of patients with regard to an excessive use of technical gear and on the other hand also to guarantee a clearer arrangement of medical apparatus' for medical personnel. In particular, there are great efforts ongoing to reduce the conventionally used plurality of cables and lines in order to guarantee a clearer arrangement of the individual lines to or from the patient in order, in particular, to also exclude a possible wrong handling of medical systems by a "mixing up" of the cables and lines. In this connection, a blood pressure measurement has already been integrated into an infusion system, wherein the fact was used that the liquid column from the arterial or venous catheter (not shown) to a pressure gauge may be used as a pressure transmission medium when a sufficiently form-stable tube between venous/arterial catheter and pressure gauge is used. The blood pressure is then transmitted via the infusion solution from an artery or vein via the catheter and via the so-called form-stable tube to a special sensor which is implemented to detect pressure variations in the infusion solution which then correspond to the blood pressure values to be measured. Such a pressure sensor is also called a transducer.

Figure 3:
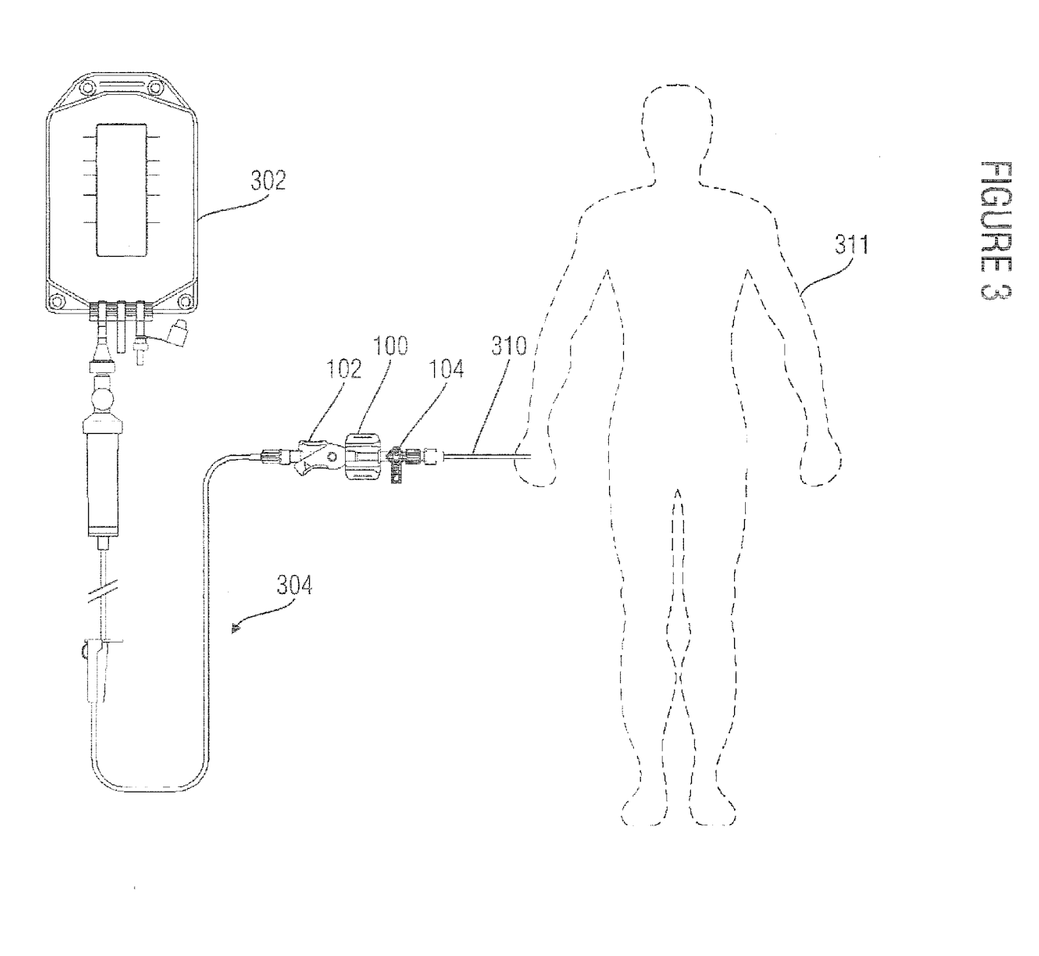
FIG. 3 shows a schematical illustration of a setup of an infusion system with pressure measurement.

The basic setup of such an infusion system with the functionality of a blood pressure measurement is illustrated in FIG. 3. Such a system comprises an infusion solution bag 302 which is connected to a first tap or rinsing system 102 via an infusion solution tube 304. The rinsing system is provided with a capillary serving as a pressure decoupling of the further system components from the infusion solution bag 302. The rinsing system 102 may here be designed such that it guarantees a predefined flow rate of, for example, 3 ml per hour.

The first tap or the rinsing system 102, respectively, is connected to a transducer 100 which may again be connected to a second tap 104. The second tap 104 is connected to the patient 311 via a pressure-stable pressure measurement line 310 (for example via a catheter). Here it is to be noted, that that the pressure measurement line 310 illustrated in FIG. 3 should comprise a high form stability or rigidity, i.e. a low elasticity, in order not to corrupt or dampen pressure variations.

The second tap 104 is normally used for "zeroing", i.e. for setting or calibrating the pressure to be measured at the transducer 100 with respect to atmospheric pressure, by providing the tap 104 of the transducer 100 with atmospheric pressure while decoupled from the patient.

A known type of transducer in pressure measurement systems consists of several individual parts. A typical setup of such a conventional transducer is given in the sectional view in FIG. 4.

Figure 4:
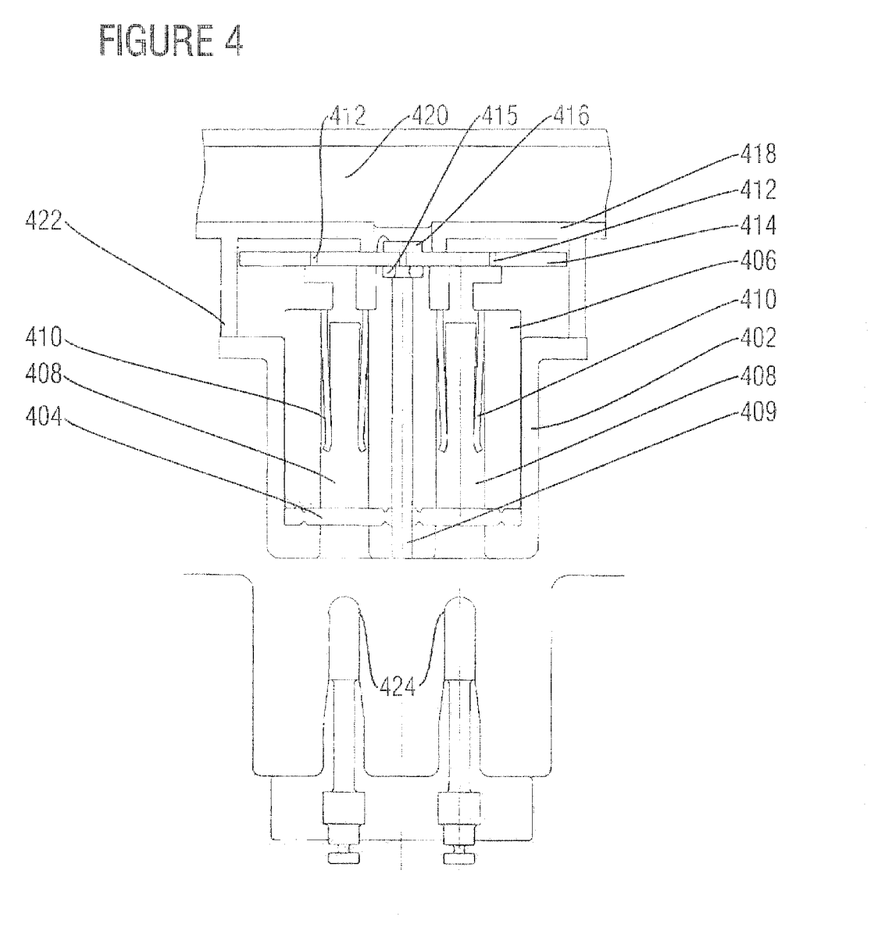
FIG. 4 shows a sectional illustration of a conventional transducer.

According to FIG. 4, the conventional transducer comprises a bottom housing part 402 (for example in cup shape), in which a pre-formed membrane 404 (for example made of silicon) is inserted. Onto the membrane 404 a contact carrier 406 is seated, comprising openings 408 into which socket contacts 410 with contact springs are pressed.

Further, the bottom housing part 402, the membrane 404 and the contact carrier 406 comprise a central hole 409, through which an atmospheric pressure of the exterior environment of the transducer is applied to a top area of the contact carrier 406.

The contact springs are soldered to terminal contacts 412 on the ceramic plate 414, wherein the contact terminals 412 are connected to contacts of a measurement chip 416. The measurement chip 416 is here arranged on a first side of the ceramic plate 414 above an opening in the ceramic plate 414, which is part of the central hole 409, wherein the terminal contacts 412 are arranged at a second side of the ceramic plate 414 opposite the first side.

Further, an O-ring 415 is arranged between the contact carrier 406 and the ceramic plate 414 laterally surrounding the opening 409 in the contact carrier 406. Hereby, for an atmospheric pressure compensation, an ambient air pressure is applied to the measurement chip 416 as a reference value via the central hole 409 or the opening in the ceramic plate 414, respectively. Further, by the O-ring 415 a sealing of the socket contacts or the electric connections, respectively, like the terminal contacts 412 or conductive traces on the ceramic plate 414, against conductive liquids is provided, like for example the infusion solution or liquids applied from the outside, which might enter into the interior of the housing when connecting the transducer.

Further, the transducer comprises a top housing part 418 including a flow channel 420 for the infusion solution. The measurement chip 416 is here arranged in a recess of the flow channel 420. In addition, the measurement chip is covered by a gel, protecting the measurement chip 416 against the infusion solution, as with a direct contact of the electrically conductive infusion solution with the measurement chip 416 a corruption of the measurement results by "creeping currents" would occur in the electrically conductive infusion solution. Via the gel, however, pressure variations may be transmitted in the fluid to the measurement chip 416. Further, the top housing part 418 is connected to the bottom housing part 402 at welding or splice points 422 (for example via an ultrasonic welding), so that the transducer in its final form is produced.

A connection of the transducer is now performed such that a socket or a socket connection 424, respectively, is passed via an opening into the floor of the bottom housing part 402 through the membrane 404 and brought into connection with the contact springs of the socket contacts 410 in an electrically conductive way. For this process, for example, the membrane 404 is already provided with slots, which strip off possibly present liquids at the socket pins when plugging in the connection plug 424.

Due to the high number of individual parts, the manufacturing process for the type of transistor illustrated in FIG. 4 is cost- and time-consuming. A possible manufacturing process here, for example includes the following steps.

First of all, in the manufacturing of a transducer, the socket contacts 410 are pressed into the contact carrier 406. Subsequently, the O-ring 415 is seated onto this contact carrier 406 provided with the socket contacts 410, whereupon the ceramic plate 414 (hybrid ceramic with imprinted conductive traces and resistances) is put onto the O-ring 415. The measurement chip 416 is attached to the ceramic place 414 with the corresponding terminal contacts 412. After seating the hybrid ceramic onto the O-ring 415 and the contact carrier 406, soldering tags 411 of the socket contacts 410, pressed into the contact carrier, are connected and soldered to the terminal contacts 412 of the hybrid ceramic. Due to the high temperatures occurring during soldering, the contact carrier 414 has to be manufactured from an especially temperature- and form-stable material, which is cost- and time-consuming and also limits the selection of material candidates with respect to other desired material characteristics. After the contacting, the membrane 404, for example as a sealing membrane made of silicon material, is inserted into the bottom housing part 402, in order to be clamped in between the contact carrier 406 and the bottom housing part 402. By this, the socket contacts 410 pressed into the contact carrier 406 are additionally sealed from the bottom. The membrane 404 is here a pre-manufactured silicon membrane which is used as an individual part in the manufacturing of such a transducer. Hereupon, a joining of the bottom housing part 402 with a top housing part 418 is performed, GO whereby the membrane 404 is clamped in, as described above. The bottom housing part 402 may be welded to the top housing part 418 using ultrasonics at the welding spot 422 or also be connected to the top housing part 418 using adhesives or solvents. Welding using ultrasonics enables a high tightness of the connection, is very cost- and times consuming, however, as a tight connection of the top housing part 418 and the bottom housing part 402 of the transducer has to be guaranteed, so that no liquid may enter into the transducer housing. This could lead to an electrical connection between the contacts and to a drift of the pressure measurement signal. Thus, it is required to perform a special examination of the tightness between the top housing part 418 and the bottom housing part 402, which is time-consuming and in particular in mass production of such transducers also costly. Finally, a gel is filled into the recess of the flow channel 420 to seal the sensor 416 watertight against the infusion solution, however to simultaneously enable a pressure transmission from the fluid in the flow channel 120 to the sensor 416. This filling in may, however, due to reasons of manufacturing technology, only take place by means of a cost- and time-consuming method using a syringe through the flow channel 120.

SUMMARY OF THE INVENTION

It is thus the object of the present invention to provide a component for inserting a fluid pressure measurement unit and a method for manufacturing a component of a fluid pressure measurement unit which enable a less cost- and time-consuming way of manufacturing, respectively.

According to a first aspect, the present invention provides a method for manufacturing a component of a fluid pressure measurement unit, with the steps of:

providing a measurement element with a measurement chip arranged on a first side of the chip carrier and a plurality of socket-shaped terminal contacts for contacting contact terminals of the measurement chip, wherein the socket-shaped terminal contacts protrude from a second side of the chip carrier opposite from the first side of the chip carrier;

providing a housing element comprising a plurality of receiving holes in a first side of the housing element which are implemented to receive the socket-shaped terminal contacts when combining the housing element with the measurement element, wherein the receiving holes extend from the first side of the housing element to a second side of the housing element opposite from the first side of the housing element, wherein providing the housing element includes spraying on a sealing element to the first side of the housing element and/or spraying on a closing element to the second side of the housing element for closing the receiving holes on the second side of the housing element; and combining the measurement element and the housing element such that the second side of the chip carrier is opposite from the first side of the housing element and the socket-shaped terminal contacts are arranged in the receiving holes to manufacture the component of the fluid pressure measurement unit.

According to a second aspect the present invention provides a method for manufacturing a component of a fluid pressure measurement unit, with the steps of:

providing a measurement element with a measurement chip arranged on a first side of a chip carrier and a plurality of socket-shaped terminal contacts for contacting contact terminals of the measurement chip, wherein the socket-shaped terminal contacts protrude from a second side of the chip carrier opposite from the first side of the chip carrier, wherein the step of providing the measurement element includes electrically connecting soldering terminals of the socket-shaped terminal contacts to the contact terminals of the measurement chip by soldering;

providing a housing element comprising a plurality of receiving holes in a first side of the housing element which are implemented to receive the socket-shaped terminal contacts when combining the housing element with the measurement element, wherein the receiving holes extend from the first side of the housing element to a second side of the housing element opposite from the first side of the housing element; and subsequently combining the measurement element and the housing element such that the second side of the chip carrier is opposite from the first side of the housing element and the socket-shaped terminal contacts are arranged in the receiving holes to manufacture the component of the fluid pressure measurement unit.

According to a third aspect, the present invention provides a method for manufacturing a fluid pressure measurement unit, with the steps of:

performing one of the above-mentioned methods;

providing a fluid channel terminal element comprising a fluid pressure measurement volume with a terminal opening for fluidically coupling the measurement element or for fluidically coupling a gel surrounding the measurement chip to the fluid pressure measurement volume; and connecting the component of the fluid pressure measurement unit to the fluid channel terminal element such that a pressure transmission from a fluid located in the fluid pressure measurement volume to the measurement chip is enabled.

According to a fourth aspect, the present invention provides a component for being used in a fluid pressure measurement unit, the component having:

a housing element having a plurality of receiving holes extending from a first side of the housing element to a second side of the housing element opposite from the first side of the housing element, wherein the housing element comprises a sealing element at the first side which is integrally connected to the housing element, wherein a material of the sealing element is different from a material of the housing element, and/or wherein the housing element comprises a closing element on the second side for closing the receiving openings at the second side of the housing element which is integrally connected to the housing element, wherein the material of the closing element is different from a material of the housing element; and a measurement element with a measurement chip arranged on a first side of a chip carrier and a plurality of socket-shaped terminal contacts for contacting contact terminals of the measurement chip, wherein the socket-shaped terminal contacts protrude from a second side of the chip carrier opposite from a first side of the chip carrier, wherein the measurement element and the housing element are constructed such that the measurement element and the housing element are capable of being combined such that in a combined state the socket-shaped terminal contacts protrude into the receiving holes and the second side of the chip carrier is opposite from the first side of the housing element, in order to form the component for being used in the fluid pressure measurement unit.

The present invention is first of all based on the finding that a substantially more simple or less costly manufacturing is enabled when the necessity of using a cost-intensive and temperature- and form-stable material for the socket contact receptacle or the contact carrier, respectively, into which the socket contacts are pressed, is omitted.

According to one aspect of the present invention, the above finding is extended by the finding, that the freer selection of the material for the socket contact receptacle enables integrally forming the socket contact receptacle and the bottom housing part, as also a moulding of the sealing element (for example as a replacement of the O-ring) to the first side of the housing element and/or a moulding of the closing element (for example replacing the silicon membrane) to the second part of the housing elements is enabled. This again means a substantial simplification when assembling the component to be manufactured of the fluid pressure measurement unit, as in this case the number of individual parts to be processed may be clearly reduced. This results from the fact that moulding the sealing elements or the closing elements, respectively, may be performed substantially more effectively with regard to method technology and automation than a manually (or also automatically) performed assembly of the component of the fluid pressure measurement unit from a plurality of individual parts. Preventing a separate O-ring and the membrane on the second side of the housing element thus enables, for example, the omission of at least one manufacturing step when assembling the component of the fluid pressure measurement unit.

In other words, the above approach offers the advantage that by the omission of using a great number of individual parts, like, e.g., the O-ring and/or the silicon membrane, a cost reduction due to saving manufacturing steps is possible. The bottom part of the housing may be manufactured integrally as the housing element with the sealing element and the closing element, whereby individual manufacturing steps for manufacturing or provisioning, respectively, the housing element may be prevented (like for example inserting the predetermined contact carrier into the bottom housing part). Such an approach offers the advantage that now a sealing membrane plate does not have to be accurately inserted into the bottom housing part in an individual, cost- and time-consuming manufacturing step, onto which the contact carrier is placed, but that the sealing membrane for sealing the receiving holes in the housing element may be manufactured by simply moulding it on. By this, again, a cost reduction may be realized by the use of a more simple manufacturing step than a step of pre-fabricating the sealing membrane and inserting the pre-fabricated sealing membrane.

A further aspect adds to the above underlying finding by the fact that it was found out that the free selection of the material for the socket contact receptacle or the bottom housing part, respectively, may be enabled when the socket contacts are mounted onto the ceramic plate before inserting the socket contacts into the socket contact holes, whereby for the bottom housing part also the use of a material for the housing element is possible which does not require such high temperature- and form-stability requirements and is more advantageous in a different regard, like, e.g., with regard to the costs when using materials with high temperature- and form-stability.

According to a preferred embodiment of the inventive method, the step of provisioning the housing element includes forming a central opening between the receiving holes, wherein the central opening extends from the first side of the housing element to the second side of the housing element, wherein the step of provisioning the measurement element includes provisioning an opening in the chip carrier below the measurement chip, and wherein the step of joining by means of the measurement element with the housing element is performed such that central opening is in connection with the opening of the chip carrier and the measurement chip is fluidically connected to an exterior environment of the component of the fluid pressure measurement unit. Hereby, it is possible to perform a calibration of the measurement chip with an ambient air pressure, so that the transducer may be advantageously used in the different application scenarios.

Further, the step of provisioning the measurement element may include attaching a sensor dome at the first side of the chip carrier, wherein the sensor dome surrounds the measurement chip and wherein the step of provisioning further includes filling the sensor dome with a gel such that the measurement chip is covered by the gel. This offers the advantage that the gel may be filled already before joining the component of the fluid pressure measurement unit or at least before attaching to the flow channel, and a complicated and thus time-consuming filling of the gel onto the measurement chip via the fluid channel is not required any more.

In a further preferred embodiment of the present invention, the step of provisioning the housing element includes moulding the closing element, wherein the provisioning of the housing element further includes forming contacting holes in the closing element in the region of the receiving holes. The contacting holes may here be implemented as throughput holes. The provisioning of the holes here offers the advantage that no pre-slotting of the closing element and no uncontrolled ripping of the closing element when plugging in contact pins for contacting the transducer is to be feared. Further, a ring- or circular-shaped implementation of the contacting holes offers the advantage, that by such forms the contact pins are stripped off of contaminating liquids, like, e.g., sodium chloride solution, in a better way and the interior space of the housing may be sealed better so that, for example, an entering of liquids like the infusion solution into the receiving holes or the socket-shaped terminal contacts located therein is prevented and thus also no corruption of the measurement results by leakage currents has to be feared. A blind hole offers the advantage, that the interior of the opening with the socket-shaped terminal contacts is not contaminated during transport or in general after the manufacturing up to the first use. Further, forming the hole may not only be performed by cutting or punching, but also by direct shaping during moulding, which requires no additional costs or no extra step, respectively. Further, a pre-slotted blind hole may be used which seals in an annular form, wherein simultaneously the slotted part is liquid-tight in the unplugged state.

In a further preferred embodiment, the step of provisioning the housing element includes forming a base body with the receiving holes made of a thermoplastic material, like, e.g., a polyolefin or another plastic material suitable for moulding with another material, and moulding TPE for forming the sealing element and/or the closing element. Such a material combination for the moulded elements and the housing element offers the advantage of an especially well adhering connection of the moulded elements to the housing element.

Further, in one embodiment of the inventive method, the step of provisioning may include moulding a sealing element, wherein the step of provisioning the housing element further includes moulding a further sealing element separate from the sealing element to the first side of the housing element. For example, also the step of moulding may include moulding on of a sealing lip to a connection area between the housing element and a fluid channel terminal element. Providing such a moulded and preferably circumferential sealing lip to the fluid channel terminal element offers the advantage of a constructively simple implementation of a sealing between a top and a bottom partial element of the fluid pressure measurement unit, so that, for example, a cost- and time-consuming welding by ultrasonics and a subsequent separate examination are not necessary any more. This may in particular be advantageous when the top partial element, i.e. the fluid channel terminal element, and the bottom partial element, i.e. the housing element, are connected by a simple compression, like it would, for example, be possible using a snap-on device. Further, accordingly a screw closure may be used. It is the aim of such a seal to seal off the top partial element from the bottom partial element, independent of a sealing to the fluid channel. This way, either using the snap-on connection or using the screw closure, simple mounting possibilities may be realized which are clearly more cost-effective than the conventional ultrasonics-based welding. At the same times however, it is also guaranteed that a tightness between the top and bottom partial element of the fluid pressure measurement unit is guaranteed.

The fluid channel terminal element may comprise a fluid channel having a smaller cross-section at a location in the area of the terminal opening than at a further location, wherein in the area of the terminal opening a viewing window is arranged in a wall of the fluid channel, enabling an improved view on the measurement chip or a gel surrounding the measurement chip from outside the fluid pressure measurement unit. Such a cross-sectional distribution enables the realization of the Venturi principle, so that the fluid in the area of the terminal opening flows faster than in the area of the fluid channel at a location having a greater cross-section. In particular when the measurement sensor or the measurement chip are fluidically connected to that part of the fluid channel which has a smaller cross-section than another partial area of the fluid channel, such an arrangement offers the advantage that due to the increased flow velocity in the partial area of the flow channel fluidically connected to the measurement sensor, it may be guaranteed, that in this part no bubbles are present any more, which may have possibly settled, during the first filling of the line system or during use, at the measurement chip or at the surfaces or edges in this area. In order to provide the possibility for a user to perform a better control as to whether no bubbles have actually settled above the measurement chip, which could corrupt a measurement result, a viewing window or a lens may also be arranged directly above the measurement chip, so that an area of the flow channel which is fluidically connected to the measurement chip or a gel surrounding the measurement chip may be viewed from the outside in a magnified way.

BRIEF DESCRIPTION OF THE DRAWINGS

Preferred embodiments of the present invention will be detailed subsequently referring to the appended drawings, in which.

DESCRIPTION OF THE PREFERRED EMBODIMENTS

Figure 1A:
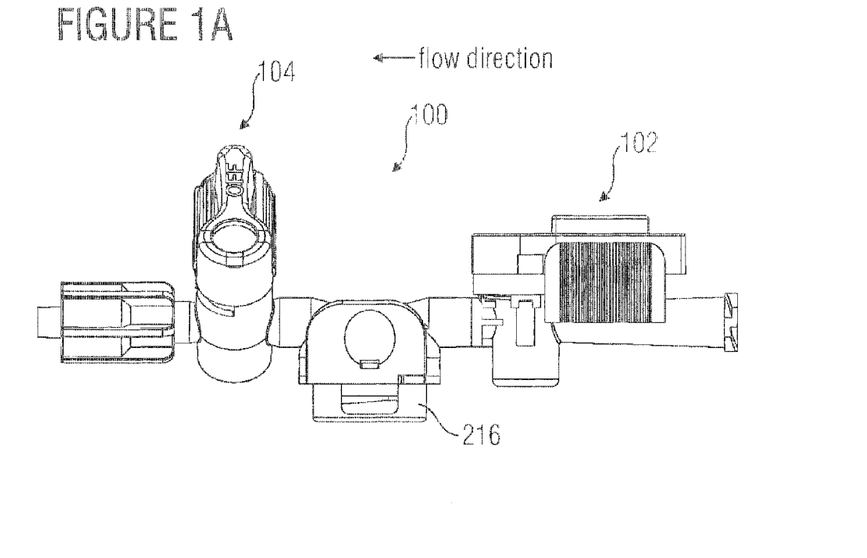
FIG. 1A shows a side view of a partial area of a pressure measurement system illustrating an embodiment of the inventive component of a fluid pressure measurement unit.

FIG. 1A shows a section from a pressure measurement system comprising a transducer or pressure gauge 100. Here, the pressure gauge 100 may be integrated into the pressure measurement system such that it is arranged in the flow direction of the infusion solution behind a rinsing system (first tap) 102 and before a second tap 104. The rinsing system 102 may be arranged towards an infusion solution reservoir, while the second tap 104 is, for example, connected between the transducer 100 and the patient. By the rinsing system 102 it may be guaranteed, that the transducer is protected from pressure variations, caused by the infusion system, and that a desired flow rate is guaranteed, while the second tap 104 may be closed when actions, like, for example, taking a blood sample, are being performed at the patient. Additionally, the second tap may be used for "zeroing" the pressure sensor against atmospheric pressure.

Also other embodiments with taps (102, 104) at both ends or completely without taps or with other tap arrangements, respectively, are possible.

Figure 1B:
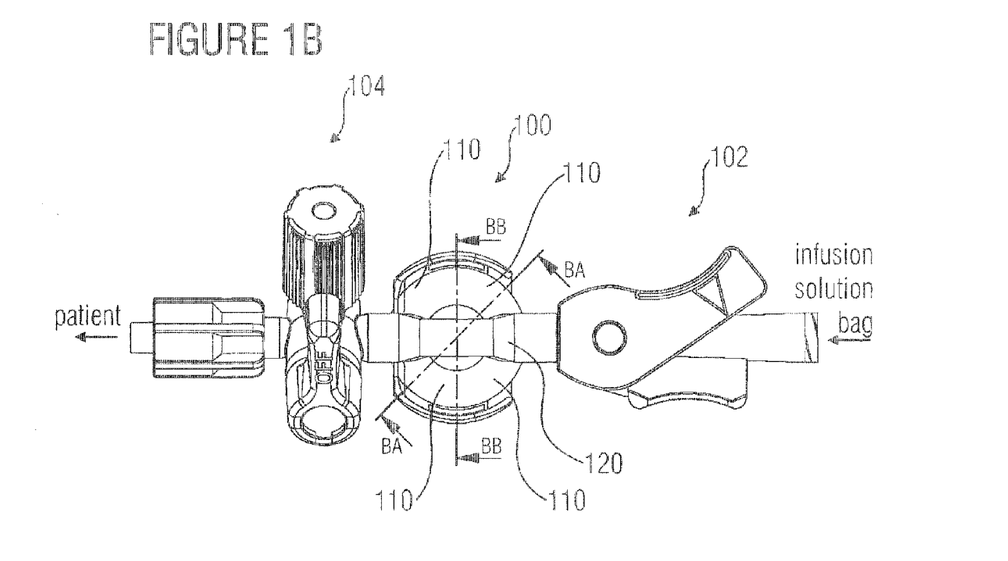
FIG. 1B shows a top view of the component of the fluid pressure measurement unit illustrated in FIG. 1A.

FIG. 1B shows the arrangement illustrated in FIG. 1A from another angle of view. Here, however, for explaining the following FIGS. 1C and 1D already two intersecting lines through the transducer 100, i.e. the first intersecting line BA-BA and the second intersecting line BB-BB, are plotted in. As it is subsequently illustrated in more detail, the section along the intersecting line BA-BA runs through two socket-shaped terminal contacts. These terminal contacts (which are not illustrated in FIG. 1B) form the terminal contacts of a Wheatstone measurement bridge, wherein, however, the two contacts illustrated in more detail along the intersecting line BA-BA in the following merely illustrate two contacts of the Wheatstone measurement bridge. Two further contacts of the Wheatstone measurement bridge are arranged diagonally to the terminal contacts located along the intersecting line BA-BA, i.e. four contacts of a Wheatstone measurement bridge are arranged in the areas 110, which is, however, not clearly visible in FIG. 1B.

Further, it is illustrated in FIG. 1B how a flow channel 120 necks in the area of the transducer 100 or the fluid pressure measurement unit, respectively, corresponding to the Venturi principle.

Further, not illustrated in FIG. 1B, however, a viewing window may be arranged in the form of a magnifying glass in the necked part of the flow channel 120, so that an optically enlarged viewable area, preferably onto the measurement chip, may be realized, whereby it may then be examined by a user of the transducer 100, whether bubbles have settled above the measurement chip in the flow channel.

Figure 1C:
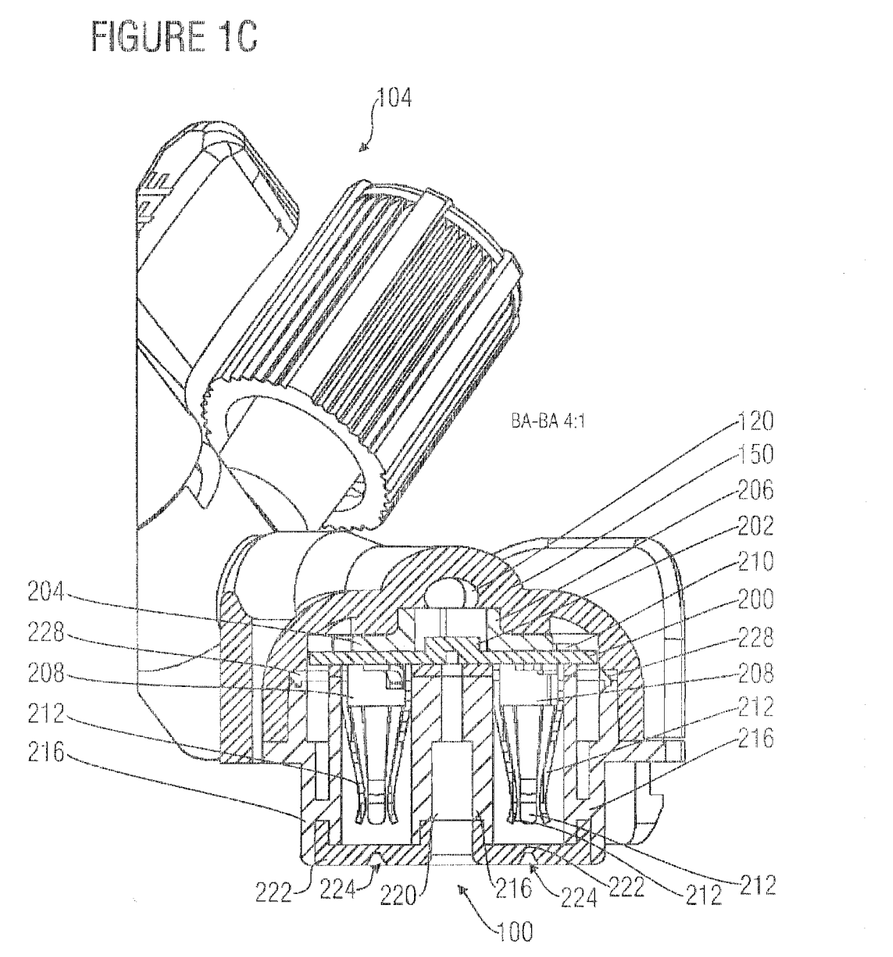
FIG. 1C shows a sectional view of the embodiment illustrated in FIGS. 1A and 1B of the component of the fluid pressure measurement unit along the intersecting line BA-BA illustrated in FIG. 1B in an enlarged illustration.
Figure 1D:
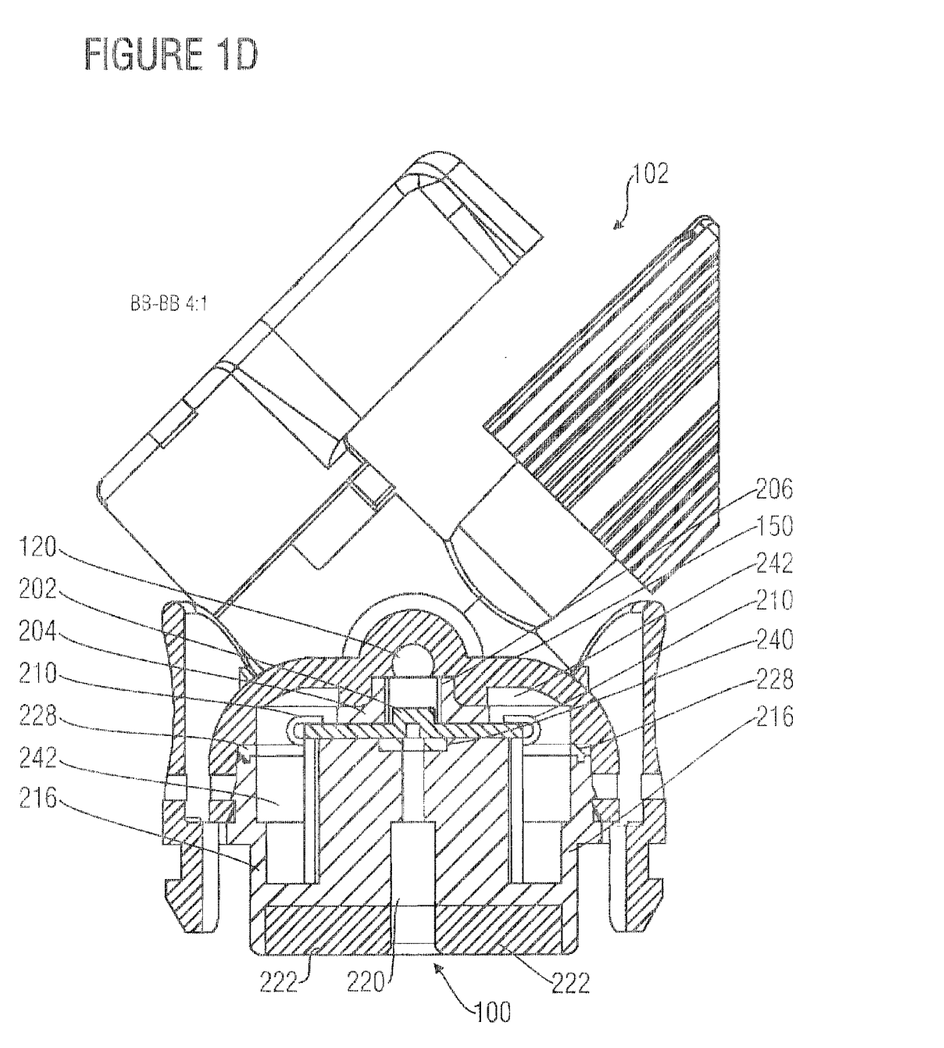
FIG. 1D shows a sectional view of the embodiment illustrated in FIG. 1B of the inventive component of a fluid pressure measurement unit along the intersecting line BB-BB in an enlarged illustration.

It may be seen from FIGS. 1C and 1D that the transducer comprises a top partial element 150 (fluid channel terminal element), forming a part of the flow channel 120 and a top housing lid of the transducer 100. Further, it may be seen from FIGS. 1C and 1D that also the interior setup of the transducer 100 is constituted of a plurality of components which are to be described in more detail for illustrating reasons with reference to FIG. 2.

Figure 2:
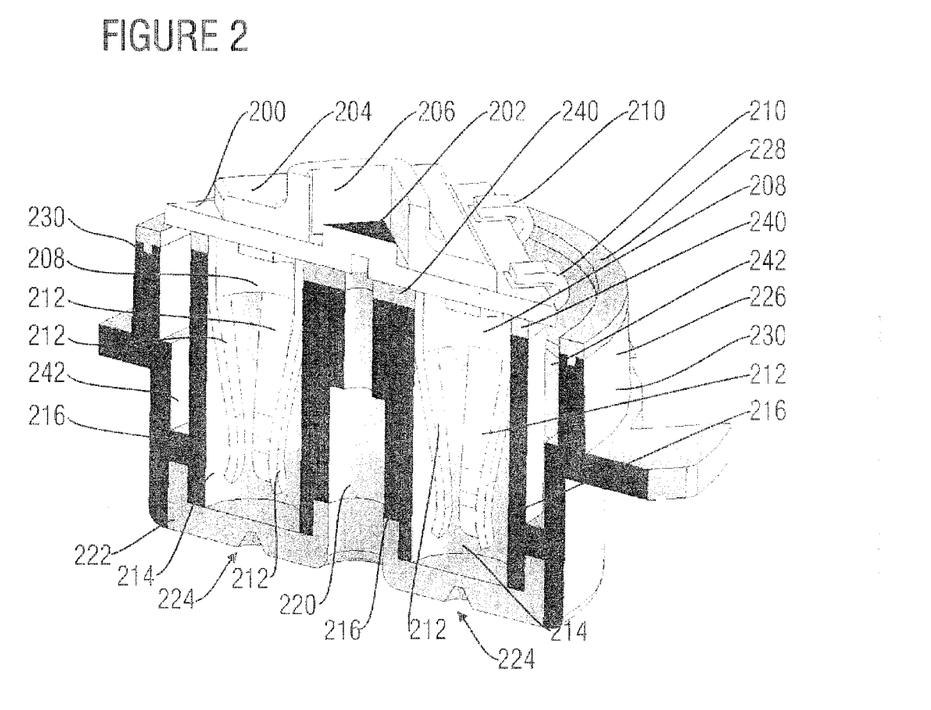
FIG. 2 shows an enlarged perspective sectional illustration of the bottom housing part or the bottom partial element, respectively, of the fluid pressure measurement unit of FIG. 1A-1D.

FIG. 2 shows a perspective sectional illustration of a part of the transducer 100, as it is illustrated in FIG. 1C. In particular, in FIG. 2 the assembled or completed bottom partial element of the transducer 100 is shown, respectively. For reasons of clarity, in the following first of all the setup of the bottom partial element illustrated in FIG. 2, i.e. of the housing element, is explained, whereupon its manufacturing is explained with reference to one embodiment.

The bottom element of the transducer 100, illustrated in FIG. 2, comprises in its completed state a chip carrier 200, at whose first side a sensor 202 is arranged or mounted, respectively. The chip carrier 200 may be a hybrid ceramic with imprinted conductive traces and resistances. For the sensor 202, for example, an integrated circuit (chip) may be used. In order to protect the sensor 202, also at the first side of the chip carrier 200 a sensor dome 204 is arranged, so that a wall of the sensor dome 202 protruding from the chip carrier 200 surrounds the sensor 202. A gel filling is not illustrated, which is, for example, filled into a recess 206 formed by the sensor dome 204 and the chip carrier 200, in which the sensor 202 is located, in order to cover the sensor 202. Further, the bottom partial element illustrated in FIG. 2 comprises socket contacts 208 having soldering tags 210 and contact springs 212. The soldering tags may either extend to the first side of the chip carrier or only extend to the second side of the chip carrier. In FIG. 2, only the former possibility is illustrated. The sensor dome is preferably filled with a gel, sealing the sensor 202 from the fluid channel in a fluid-tight way, however, enabling a pressure transmission. The socket contacts 208 are here arranged on a second side opposing the first side of the chip carrier 200. Further, the socket contacts are respectively arranged in an opening 214 of the bottom housing part 216. The opening 214 of the bottom housing part 216 extends from a first side of the bottom housing part up to a second side opposite the first side of the bottom housing part 216. In the bottom housing part 216, further a central opening 220 is arranged, serving as a vent hole for the sensor chip 202. For sealing the vent hole 220, at the bottom housing part 216 a sealing element 240 is moulded. Further, the openings 214 in the bottom housing part 216 are closed on the second side of the contact carrier by a moulded sealing membrane 222, for example made of a TPE (TPE=thermoplastic elastomer). Further, the moulded sealing membrane 222 comprises a blind hole 224 in the central area. With a blind hole, the closed area may be punched to enable a passage. Alternatively, also a through hole may be formed in the moulded sealing membrane 222, which is not illustrated in FIG. 2, however.

Further, the bottom housing part 216 may comprise a moulded sealing 228 at a transition 226, serving as a sealing lip when combining or connecting, respectively, the bottom partial element illustrated in FIG. 2 with the top partial element 150 of the transducer illustrated in FIG. 1C or 1D, respectively. The sealing lip 228 may here preferably also consist of TPE, so that the bottom housing part may be manufactured integrally with all required sealing elements. Also the sealing element 240 operating as a replacement of the O-ring may be manufactured from a TPE material.

For manufacturing the component of the fluid pressure measurement unit, now first of all the chip carrier 200 is provided with the measurement chip 202 arranged thereon and the socket contacts 208 comprising the soldering tags 210. The soldering tags are soldered to contact terminals on the chip carrier 200, wherein the contact terminals enable contacting the chip 202 arranged on the chip carrier 200 or are connected to corresponding chip pads in an electrically conductive way, respectively. Soldering is here performed under bending or with already pre-bent soldering tags 210, such that the socket contacts 208 protrude from the chip carrier at a second side of the same, while the chip 202 and the contact terminals are arranged on the opposing first side of the chip carrier 200. Alternatively, the chip carrier may also be provided with conductive traces or through connections, respectively, such that the contact terminals 210 are arranged on the second side of the chip carrier.

Further, the sensor dome 204 may be mounted (for example adhered) to the side of the chip carrier 200, on which the sensor 202 is arranged. Finally, a filling of the sensor dome is preferably performed with a gel, such that the gel surrounds the measurement chip 202 (in FIG. 2, the gel is not illustrated in the sensor dome for reasons of clarity). By the gel, the measurement chip 202 may now be "packed" in a fluid-tight way, so that no conductive liquid, like, for example, the infusion solution, gets into direct contact with a measurement chip or with conductive traces on the chip carrier 200, respectively, and does not lead to a corruption of the measurement values. Up to this point, a measurement element consisting of the chip carrier 200, the sensor 202, the socket contacts 208 and the sensor dome 204 and the gel filling has been manufactured.

In a following or also parallel step, the sealing lip 228, a sealing membrane 222 and/or a sealing 240 may be moulded to the bottom partial element 216 in a connecting area. Many different variants for such a moulding are available, which may in particular also be used at low costs.

The measurement element created as described above, consisting of the chip carrier 200, the sensor 202, the socket contacts 208 and the sensor dome 204 with the filling of the sensor dome is then connected to the bottom partial element 216, for example pressed in. Here, the socket contacts 208 may be directly inserted into the openings 214, from which the setup illustrated in FIG. 2 results. Alternatively, however, also a loose insertion of the measurement element into the housing element may be performed, so that the socket contacts in the openings 214 have a bit of clearance, wherein a pressing and thus a sealing of the sealing element 240 to the chip carrier 200 is performed by a subsequent pressing together of the housing element 216 to the fluid channel terminal element 150, not illustrated in FIG. 2. By this, the component of the fluid pressure measurement unit is manufactured.

The thus manufactured component of the fluid pressure measurement unit is provided to be attached to the top partial element 150 (i.e. the fluid channel terminal element), so that the sensor 202 is fluidically connected to the flow channel 120 via the gel filling and pressure variations of a fluid in the flow channel 120 are transmitted to the measurement chip 202 via the gel filling. The adhesive or bonding area, respectively, between the measurement element and the top partial element 150 may here, for example, be located between the sensor dome 204 and the top partial element 150 and guarantee a sealing of an intermediate space 242 in the bottom partial element.

Connecting the top partial element 150 to the bottom partial element 216 may, for example, be performed by gluing or bonding, respectively, such that an exterior side wall 230 illustrated in FIG. 2 is provided with glue material and joined with the transducer lid or channel top 150, respectively, illustrated in FIGS. 1C and 1D. Alternatively, however, also a snap-on closure or a screw closure may be used, wherein by pressing together the top and bottom partial elements and the pressing together of the sealing lip 228 connected therewith, a fluid-tight connection between these two partial elements and a sealing of the interior 242 results. It is to be noted, however, that with a screw closure the sensor dome 204 should not be square-shaped as illustrated in FIG. 2, but be implemented in a circular shape. Such a combination possibility either by bonding or by a mechanical connection, like a snap-on or screw closure connected with the fact that the bottom housing part 216 was preferably already provided with all sealings, thus offers a very simple and cost-effective possibility to manufacture the transducer 100.

The above-explained embodiment of the inventive method offers the advantage that no socket contacts have to be pressed into the contact carrier any more, no O-ring is put onto the contact carrier and subsequently the chip carrier in the form of the hybrid ceramic is not placed onto the soldering tags and soldered, which would have a high thermal or stability-straining effect on the contact carrier.

Further, an advantage reqarding costs may be realized by the integral manufacturing of the bottom housing part 216 with all required sealings in the two-component process.

Here, a sealing element 240 comparable to the O-ring may be realized between the contact carrier or the bottom housing part 216, respectively, on the one hand, and the chip carrier 200 on the other hand, like it is, for example, possible with the sealing element 240 illustrated in FIG. 2. This sealing element 240 may serve for sealing off the socket contacts 208 from the interior 242. Further, also the sealing element 240 may serve as a sealing between the cavity formed by the central hole 220 and the chip carrier 200, so that the interior 242 and the socket contacts 208 in the bore holes 2 are sealed off from each other and from the central hole 220. By this it is guaranteed that also, for example, with a leakiness of the infusion system with infusion solution escaping, no such conductive infusion solution may reach the socket-shaped terminal contacts 208 via the central hole 220 and, for example, cause a corruption of the measured signal via "leakage currents". Simultaneously, in the region of the central hole 220, further an opening in the chip carrier 200 may be provided, so that an ambient air pressure of the ambient air may directly reach a back side of the measurement sensor, whereby a calibration of the measurement sensor 202 in different environments of use is enabled, as the pressure-sensitive membrane of the sensor (not illustrated) is open or exposed, respectively, towards both sides, so that with an atmospheric pressure applied on both sides no bias of the membrane exists.

Regarding the sealing membrane 222 closing the openings 214 at the second side of the bottom housing part 216, it is to be noted, that the contacting may take place either by piercing the contact electrode through the blind hole 224 or, if the hole is implemented in the form of a through hole, the contacting may be performed by means of putting through the contact through this through hole.

Implementing the tight membrane 222 with the blind holes 224, which is to be pierced, or implementing the through holes in the sealing membrane 222 and subsequently passing through the contact electrode thus offers the advantage that, in particular in the implementation of circular blind or through holes, respectively, the usually circular contact electrodes may basically be cleaned from contamination like, for example, the conductive infusion liquid, by "stripping off", so that the probability of introducing electrically conductive contaminations to the socket-shaped terminal contacts 208 with the contact springs 212 is clearly reduced.

In summary, an approach results from the above embodiments, in which the socket contacts are directly soldered to the ceramic or the chip carrier, respectively, whereupon the ceramic is, for example, bonded to or connected to the top housing part. Pressing the socket contacts into the bottom housing part is not necessary any more. Rather, the socket contacts in the bottom housing part have a bit of clearance. As the soldering process is not in connection with the contact carrier or the bottom housing part any more, the bottom housing part may be manufactured integrally. The materials may, for example, be selected so that the bottom housing part may be manufactured as a two-component part (for example a special combination of the material of the bottom housing part (like, e.g., polypropylen) and a material for moulding the sealings (like, e.g. TPE)). Here, the bottom housing part, the contact carrier, the sealing membrane and the O-ring as well as the sealing lip are preferably implemented as a single part. In addition to that, an ultrasonic welding is not required any more, as the tightness between top and bottom housing parts may preferably be achieved by a sealing lip which is also moulded.

While this invention has been described in terms of several preferred embodiments, there are alterations, permutations, and equivalents which fall within the scope of this invention. It should also be noted that there are many alternative ways of implementing the methods and compositions of the present invention. It is therefore intended that the following appended claims be interpreted as including all such alterations, permutations, and equivalents as fall within the true spirit and scope of the present invention.

What is claimed is:

1. A method for manufacturing a component of a fluid pressure measurement unit, comprising:
   providing a measurement element with a measurement chip arranged on a first side of the chip carrier and a plurality of socket-shaped terminal contacts for contacting contact terminals of the measurement chip, wherein the socket-shaped terminal contacts protrude from a second side of the chip carrier opposite from the first side of the chip carrier;
   providing a housing element comprising a plurality of receiving holes in a first side of the housing element which are implemented to receive the socket-shaped terminal contacts when combining the housing element with the measurement element, wherein the receiving holes extend from the first side of the housing element to a second side of the housing element opposite from the first side of the housing element,
      wherein providing the housing element includes moulding a sealing element to the first side of the housing element and/or moulding a closing element to the second side of the housing element for closing the receiving holes on the second side of the housing element; and
   combining the measurement element and the housing element such that the second side of the chip carrier is opposite from the first side of the housing element and the socket-shaped terminal contacts are arranged in the receiving holes to manufacture the component of the fluid pressure measurement unit.

2. The method according to claim 1, wherein the step of providing the measurement element includes soldering soldering terminals of the socket-shaped terminal contacts to the contact terminals of the measurement chip.

3. A method for manufacturing a component of a fluid pressure measurement unit, comprising:
   providing a measurement element with a measurement chip arranged on a first side of a chip carrier and a plurality of socket-shaped terminal contacts for contacting contact terminals of the measurement chip, wherein the socket-shaped terminal contacts protrude from a second side of the chip carrier opposite from the first side of the chip carrier,
      wherein the step of providing the measurement element includes electrically connecting soldering terminals of the socket-shaped terminal contacts to the contact terminals of the measurement chip by soldering;
   providing a housing element comprising a plurality of receiving holes in a first side of the housing element which are implemented to receive the socket-shaped terminal contacts when combining the housing element with the measurement element, wherein the receiving holes extend from the first side of the housing element to a second side of the housing element opposite from the first side of the housing element; and
   subsequently combining the measurement element and the housing element such that the second side of the chip carrier is opposite from the first side of the housing element and the socket-shaped terminal contacts are arranged in the receiving holes to manufacture the component of the fluid pressure measurement unit.

4. The method according to claim 3, wherein the step of providing a housing element includes moulding a sealing element to the first side of the housing element and/or moulding a closing element to the second side of the housing element for closing the receiving holes on the second side of the housing element.

5. A method according to claim 1, wherein the step of providing the housing element includes forming a central opening between the receiving holes, wherein the central opening extends from the first side of the housing element to the second side of the housing element, wherein the step of providing the measurement element includes providing an opening in the chip carrier below the measurement chip, and wherein the step of combining the measurement element with the housing element is performed such that the central opening is in connection with the opening of the chip carrier and the measurement chip is fluidically connected to an exterior environment of the component of the fluid pressure measurement unit.

6. The method according to claim 1, wherein the step of providing the measurement element includes attaching a sensor dome to the first side of the chip carrier, wherein the sensor dome surrounds the measurement chip and wherein the step of providing further includes a filling of the sensor dome with a gel such that the measurement chip is covered by the gel.

7. The method according to claim 1, wherein the step of providing the housing element includes moulding the closing element, wherein providing the housing element further includes forming contacting holes in the closing element in the region of the receiving holes.

8. The method according to claim 1, wherein the step of providing the housing element includes forming a base body with the receiving holes made of a thermoplastic material and moulding a thermoplastic elastomer for forming the sealing element and/or the closing element.

9. The method according to claim 1, wherein the step of providing the housing element includes moulding a sealing element, wherein the step of providing the housing element further includes moulding a further sealing element separate from the sealing element to the first side of the housing element.

10. A method for manufacturing a fluid pressure measurement unit, comprising:
   performing a method for manufacturing a component of a fluid pressure measurement unit, comprising:
      providing a measurement element with a measurement chip arranged on a first side of the chip carrier and a plurality of socket-shaped terminal contacts for contacting contact terminals of the measurement chip, wherein the socket-shaped terminal contacts protrude from a second side of the chip carrier opposite from the first side of the chip carrier;
      providing a housing element comprising a plurality of receiving holes in a first side of the housing element which are implemented to receive the socket-shaped terminal contacts when combining the housing element with the measurement element, wherein the receiving holes extend from the first side of the housing element to a second side of the housing element opposite from the first side of the housing element, wherein providing the housing element includes moulding a sealing element to the first side of the housing element and/or moulding a closing element to the second side of the housing element for closing the receiving holes on the second side of the housing element; and combining the measurement element and the housing element such that the second side of the chip carrier is opposite from the first side of the housing element and the socket-shaped terminal contacts are arranged in the receiving holes to manufacture the component of the fluid pressure measurement unit;

performing a method for manufacturing a component of a fluid pressure measurement unit, comprising:

providing a measurement element with a measurement chip arranged on a first side of a chip carrier and a plurality of socket-shaped terminal contacts for contacting contact terminals of the measurement chip, wherein the socket-shaped terminal contacts protrude from a second side of the chip carrier opposite from the first side of the chip carrier, wherein the step of providing the measurement element includes electrically connecting soldering terminals of the socket-shaped terminal contacts to the contact terminals of the measurement chip by soldering;

providing a housing element comprising a plurality of receiving holes in a first side of the housing element which are implemented to receive the socket-shaped terminal contacts when combining the housing element with the measurement element, wherein the receiving holes extend from the first side of the housing element to a second side of the housing element opposite from the first side of the housing element; and subsequently combining the measurement element and the housing element such that the second side of the chip carrier is opposite from the first side of the housing element and the socket-shaped terminal contacts are arranged in the receiving holes to manufacture the component of the fluid pressure measurement unit;

providing a fluid channel terminal element comprising a fluid pressure measurement volume with a terminal opening for fluidically coupling the measurement element or for fluidically coupling a gel surrounding the measurement chip to the fluid pressure measurement volume; and connecting the component of the fluid pressure measurement unit to the fluid channel terminal element such that a pressure transmission from a fluid located in the fluid pressure measurement volume to the measurement chip is enabled.

11. The method according to claim 10, wherein the step of connecting the component of the fluid pressure measurement unit includes pressing the measurement element to the housing element.

12. The method according to claim 10, wherein providing the fluid channel terminal element includes providing a fluid channel comprising a smaller cross-section at a location in the region of the terminal opening than at a further location, and wherein in the region of the terminal opening a viewing window is implemented in a wall of the fluid channel such that a view on the measurement chip or a gel covering the measurement chip from outside the fluid pressure measurement unit is enabled.

13. A component for being used in a fluid pressure measurement unit, the component comprising:

a housing element having a plurality of receiving holes extending from a first side of the housing element to a second side of the housing element opposite from the first side of the housing element, wherein the housing element comprises a sealing element at the first side which is integrally connected to the housing element, wherein a material of the sealing element is different from a material of the housing element, and/or wherein the housing element comprises a closing element on the second side for closing the receiving openings at the second side of the housing element which is integrally connected to the housing element, wherein the material of the closing element is different from a material of the housing element; and a measurement element with a measurement chip arranged on a first side of a chip carrier and a plurality of socket-shaped terminal contacts for contacting contact terminals of the measurement chip, wherein the socket-shaped terminal contacts protrude from a second side of the chip carrier opposite from a first side of the chip carrier, wherein the measurement element and the housing element are constructed such that the measurement element and the housing element are capable of being combined such that in a combined state the socket-shaped terminal contacts protrude into the receiving holes and the second side of the chip carrier is opposite from the first side of the housing element, in order to form the component for being used in the fluid pressure measurement unit.

14. The component according to claim 13, wherein in the measurement element, via conductive traces between soldering terminals of the socket-shaped terminal contacts and the contact terminals of the measurement chip, a soldering layer is dielectrically connected.

15. The component according to claim 13, wherein the housing element includes a central opening between the receiving holes, wherein the central opening extends from the first side of the housing element to the second side of the housing element, wherein an opening is provided in the chip carrier below the measurement chip and wherein the central opening is in connection with the opening of the chip carrier and the measurement chip is connected on its back side to an exterior environment of the component of the fluid pressure measurement unit.

16. The component according to claim 13, wherein the measurement element includes a sensor dome on the first side of the chip carrier, wherein the sensor dome surrounds the measurement chip and wherein the step of providing further includes filling the sensor dome with a gel such that the measurement chip is covered by the gel.

17. The component according to claim 13, wherein the housing element comprises the closing element, wherein the housing element further comprises a plurality of contacting holes in the closing element in the area of the receiving holes.

18. The component according to claim 13, wherein the housing element comprises a base body with the receiving holes made of a thermoplastic material and a sealing element and/or a closing element made of a thermoplastic elastomer.

19. The component according to claim 13, comprising a sealing element, wherein the housing element further comprises a further sealing element on the first side of the housing element separate from the sealing element.

* * * * *